United States Patent [19]
Biller et al.

[11] Patent Number: 4,721,725
[45] Date of Patent: Jan. 26, 1988

[54] ARYL-CYCLOALKYL[B]PYRROLE DERIVATIVES

[75] Inventors: Scott A. Biller, Lawrenceville; Donald S. Karanewsky, East Windsor, both of N.J.

[73] Assignee: E. R. Squibb & Sons, Inc., Princeton, N.J.

[21] Appl. No.: 823,172

[22] Filed: Jan. 27, 1986

[51] Int. Cl.$^4$ .............. C07D 209/52; A61K 31/405; A61K 31/40
[52] U.S. Cl. .................... 514/412; 514/421; 548/483; 548/484; 548/452
[58] Field of Search .......... 548/516, 483, 484, 452, 548/453; 514/412, 421

[56] References Cited

U.S. PATENT DOCUMENTS

| | | | |
|---|---|---|---|
| 4,294,754 | 10/1981 | Smith | 260/326.27 |
| 4,496,742 | 1/1985 | Smith | 548/452 |
| 4,619,937 | 10/1986 | Butler et al. | 548/452 |

FOREIGN PATENT DOCUMENTS 0077209 4/1983 European Pat. Off. .

OTHER PUBLICATIONS

Chemical Abstracts, vol. 106 (11), 84270f.
Derwent Abstract, 85-185868/31.

*Primary Examiner*—Nicholas S. Rizzo
*Attorney, Agent, or Firm*—Lawrence S. Levinson; Burton Rodney

[57] ABSTRACT

Aryl-cyclopenta- and arylcyclohexa[b]pyrrole derivatives are provided having the structure

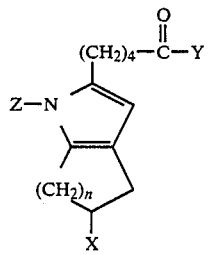

wherein n is 1 or 2;
X is —OR$^1$ or —NR$^2$R$^3$ wherein R$^1$ is H, lower alkyl, cycloalkyl, aryl, aralkyl or cycloalkylalkyl, and R$^2$ and R$^3$ may be the same or different and are H, lower alkyl, cycloalkyl, aryl, aralkyl or cycloalkylalkyl;
Y is —OR$^4$ or —NR$^5$R$^6$ wherein R$^4$ is H or lower alkyl, and R$^5$ and R$^6$ are the same or different and are H or lower alkyl; and
Z is aryl.

These compounds are useful in inhibiting the 5-lipoxygenation of arachadonic acid in RBL-1 cells and preventing leukotriene formation in macrophages and as such are useful as antiallergy agents and in treating inflammation and psoriasis.

14 Claims, No Drawings

ARYL-CYCLOALKYL[B]PYRROLE DERIVATIVES

DESCRIPTION OF THE INVENTION

The present invention relates to aryl-cyclopenta or cyclohexa[b]pyrrole derivatives which prevent leukotriene formation and as such are useful, for example, as antiallergy agents, and in treating rheumatoid arthritis and psoriasis. These compounds have the structural formula

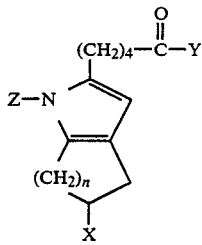

wherein n is 1 or 2;

X is —OR$^1$ or —NR$^2$R$^3$ wherein R$^1$ is H, lower alkyl, cycloalkyl, aryl, aralkyl or cycloalkylalkyl, and R$^2$ and R$^3$ may be the same or different and are H, lower alkyl, cycloalkyl, aryl, aralkyl or cycloalkylalkyl;

Y is —OR$^4$ or —NR$^5$R$^6$ wherein R$^4$ is H or lower alkyl, and R$^5$ and R$^6$ are the same or different and are H or lower alkyl; and Z is aryl.

Thus, the present invention includes compounds of the structures

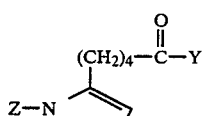 and 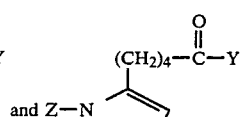

IA          IB

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or CF$_3$, an alkoxy substituent, an aryl substituent, an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or 1 or 2 lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, 1 or 2 halogens (Cl, Br or F), and/or 1 or 2 lower alkoxy groups.

The term "aralkyl", "aryl-alkyl" or "aryl-lower alkyl" as used herein refers to lower alkyl groups as discussed above having an aryl substituent, such as benzyl.

The term "lower alkoxy", "alkoxy" or "aralkoxy" includes any of the above lower alkyl, aryl or aralkyl groups linked to an oxygen atom.

The term "halogen" or "halo" as used herein refers to chlorine, bromine, fluorine or iodine with chlorine being preferred.

Preferred are those compounds of the invention wherein n is 1 or 2, Z is phenyl, Y is OH or alkoxy and X is OCH$_2$C$_6$H$_5$ or —NHC$_6$H$_5$.

The various compounds of the invention of formulae I, IA and IB may be prepared as described below.

Compounds of formula I wherein n is 1, X is OH and Y is —OR$^4$ wherein R$^4$ is lower alkyl may be prepared starting with the ketone A

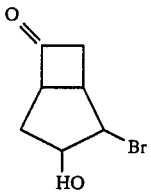

which itself is prepared by the method of Roberts: Z. Grudzinski, S. M. Roberts, *J. C. S. Perkin I,* 1975, 1767. Ketone A in solution with aqueous acetic acid is treated at reduced temperatures with hydrogen peroxide in cooled aqueous acetic acid to form lactone II

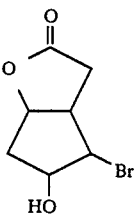

A solution of lactone II with (n—C$_4$H$_9$)$_3$SnH and azoisobutyronitrile (AIBN) in benzene is heated at reflus under an inert atmosphere, such as argon in benzene solution to form hydroxylactone III

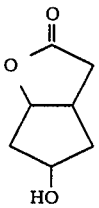

A solution of hydroxylactone III in dichloromethane under argon is treated with dihydropyran in the presence of a catalyst, such as pyridinium p-tosylate or phosphorus oxychloride to form the protected lactone IV

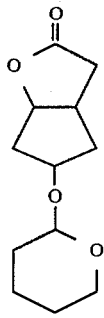

IV which is reduced to the lactol V by treating a solution of IV in dry toluene at reduced temperatures of, for example, −78° C., under argon with diisobutylaluminum hydride in heptane.

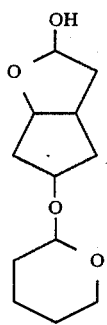

V

The lactol V is subjected to a Wittig reaction by treating a suspension of lactol V and phosphonium salt B

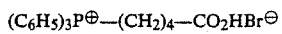

B in dry toluene at 0° C. under argon with potassium t-amyl oxide in toluene to form acid VI

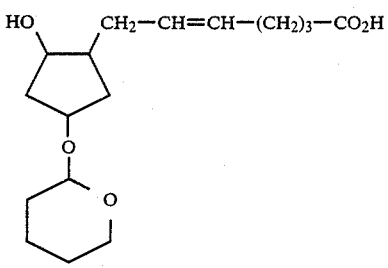

VI followed by esterification with dimethyl sulfate and potassium carbonate in refluxing acetone resulting in formation of cyclopentane VIA

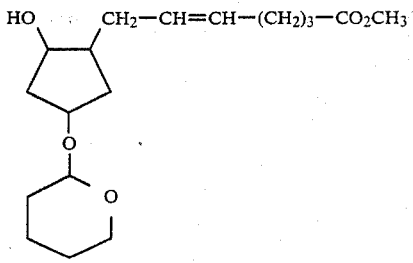

VIA

Other esters can be formed by a variety of standard methods, including the procedure of Neises and Steglich which involves treating acid VI with an alcohol ($R^4OH$) and dicyclohexyl carbodiimide and 4-dimethylaminopyridine in dichloromethane (B. Neises, W. Steglich, *Ang. Chem., Int. Ed.* 1978, 17, 522).

Ester VIA or other ester (that is, $R^4$ is an alkyl other than $CH_3$) is next made to undergo an iodo-cyclization by treating a mixture of VIA in dichloromethane and sodium bicarbonate with $I_2$ in dichloromethane to form the iodinated compound VII

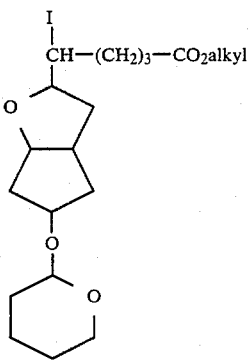

VII

The iodinated compound VII is then subjected to a dehydrohalogenation and hydration by treating a solution of the compound VII in dry benzene under argon with 1,8-diazabicyclo[5.4.0]undec-7-ene (DBU) and treating the resulting enol ether dissolved in tetrahydrofuran with aqueous acetic acid to form compound VIII

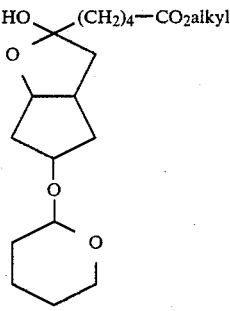

VIII

Compound VIII is then oxidized by treating a solution of VIII in dichloromethane with pyridinium chlorochromate and sodium acetate in dichloromethane to form the diketone IX

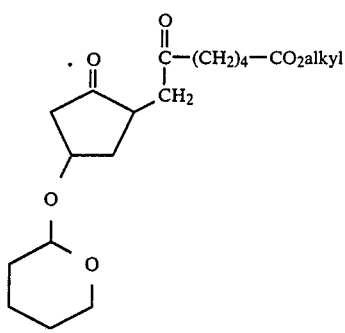

Diketone IX is then made to undergo a Pschorr pyrrole synthesis as follows:

Diketone IX in solution with chloroform or dichloromethane is reacted under argon with amine C

Z—NH₂     C such as aniline (C₆H₅NH₂) and a catalyst, such as pyridinium p-tosylate or titanium tetrachloride to form a crude mixture containing ester ID

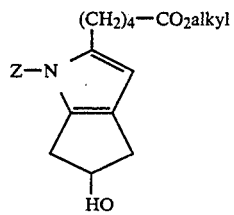

and ester IE

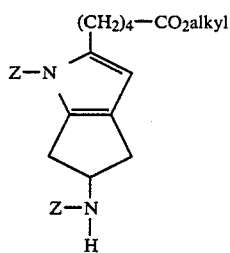

wherein the two Z groups represent the same aryl group. ID and IE may then be separated by chromatography on silica gel.

Compounds of formula I wherein X is $OR_a^1$ and $R_a^1$ is lower alkyl, cycloalkyl, aryl, aralkyl or cycloalkylalkyl is prepared starting with the lactone X

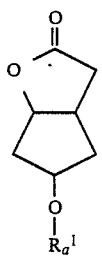

which is reduced to a lactol by treating a solution of lactone X in dry toluene at reduced temperatures of, for example, −78° C., under argon with diisobutylaluminum hydride in heptane to form lactol XI

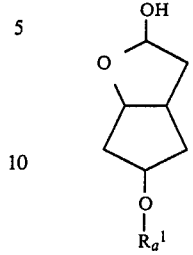

The lactol XI is subjected to a Wittig reaction by treating a suspension of lactol XI and phosphonium salt B $(C_6H_5)_3P^{\oplus}$—$(CH_2)_4$—$CO_2HBr^{\ominus}$     B in dry toluene at 0° C. under argon with potassium t-amyl oxide in toluene to form acid XII

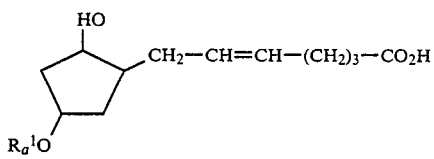

followed by esterification with dimethyl sulfate and potassium carbonate in refluxing acetone to form ester XIIA

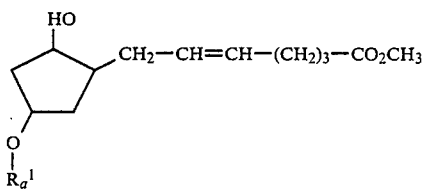

Other esters can be formed by various standard methods including the procedure of Neises and Steglich which involves treating acid XII with and alcohol (R⁴OH) and dicyclohexyl carbodiimide and 4-dimethylaminopyridine in dichloromethane (B. Neises, W. Steglich, *Ang. Chem.*, Int. Ed. 1978, 17, 522).

Methyl ester XIIA or other ester is next made to undergo an iodo-cyclization by treating a mixture of XIIa in dichloromethane and sodium bicarbonate with I₂ in dichloromethane to form the iodinated compound XIII

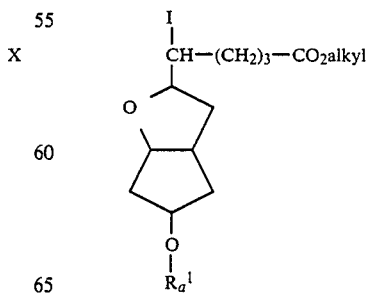

The iodinated compound XIII is then subjected to a dehydrohalogenation and hydration by treated a solution of the compound XIII in dry benzene under argon with 1,8-diazabicyclo[5.4.0]undec-7-ene (DBU) and treating the resulting enol ether dissolved in tetrahydrofuran with aqueous acetic acid to form compound XIV

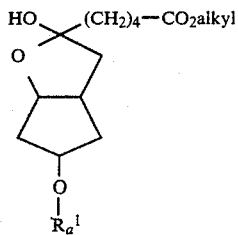

XIV

Compound XIV is then oxidized by treating a solution of XIV in dichloromethane with pyridinium chlorochromate and sodium acetate in dichloromethane to form the diketone XV

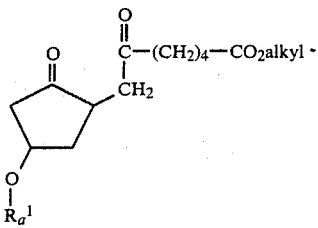

XV

Diketone XV is then made to undergo a Pschorr pyrrole synthesis as follows:

Diketone XV in solution with dry dichloromethane or chloroform is reacted under argon with amine C

Z—NH$_2$  C such as aniline (C$_6$H$_5$NH$_2$) in dry dichloromethane or chloroform and a catalyst such as pyridinium p-tosylate or titanium tetrachloride to form an ester IF

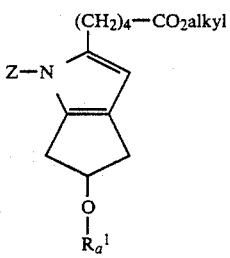

IF

The starting lactone X wherein $R_a{}^1$ is aryl may be prepared from the corresponding alcohol compound III

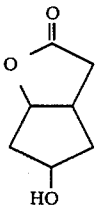

III by subjecting III to a modified Mitsunobu reaction wherein a mixture of alcohol III and alcohol D $R_a{}^1$—OH  D wherein $R_a{}^1$ is aryl in an inert solvent such as tetrahydrofuran, ether or toluene is reacted with a mixture of triphenylphosphine and diisopropylazo dicarboxylate in an inert solvent such as tetrahydrofuran, ether or toluene at reduced temperatures of from about 0° to about 25° C. to form the starting lactone XA

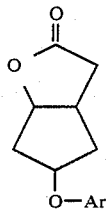

XA

The starting lactone X wherein $R_a{}^1$ is other than H or aryl, that is, $R_a{}^1$ is lower alkyl, cycloalkyl, aralkyl or cycloalkylalkyl may be prepared by subjecting alcohol III

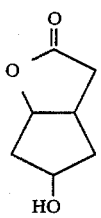

III to a Williamson ether synthesis by treating alcohol III with a base such as sodium hydride or potassium hydride in the presence of an inert solvent such as tetrahydrofuran and then treating the reaction mixture with halide E $R_a{}^1$Hal  E wherein Hal is Br, Cl or I. Where Hal is other than I, the above reaction is carried out in the presence of tetra-N-butyl ammonium iodide (n—C$_4$H$_9$)$_4$NI.

Compounds of formula I wherein n is 2 and X is O$R_a{}^1$ that is

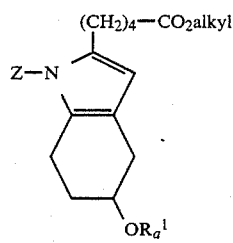

IH wherein $R_a{}^1$ is lower alkyl, arylalkyl, cycloalkyl or cycloalkylalkyl may be prepared starting with cyclohexanedione

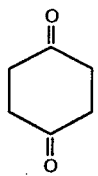

which is treated with 1,4-butanediol in the presence of p-toluenesulfonic acid and an inert organic solvent such as toluene or benzene to form ketone F

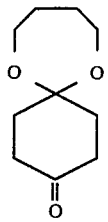

F

The above ketone was reduced to the corresponding alcohol F'

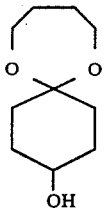

F' by reacting ketone F with lithium aluminum hydride or diisobutyl aluminum hydride in the presence of an inert solvent such as ethyl ether or tetrahydrofuran under argon, at reduced temperature of, for example, from about −20° to about 25° C. The alcohol is treated with a base such as sodium hydride, potassium hydride or potassium t-butoxide in the presence of an inert organic solvent such as tetrahydrofuran or dimethyl formamide at 0° C. to −20° C. and the mixture is then treated with a halide of the structure $R_a^1 Hal$  E (where $R_a^1$ is other than aryl)
wherein Hal is Cl, Br or I and where Hal is other than I, then tetra-N-butyl ammonium iodide is also added to form the ketal XIX

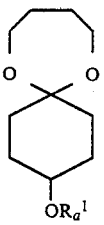

XIX

Where $R_a^1$ is aryl, the starting alcohol F' is subjected to modified Mitsunobu reaction wherein a mixture of alcohol F' and alcohol D $R_a^1 OH$  D (wherein $R_a^1$ is aryl)
in an inert solvent such as tetrahydrofuran, ether or toluene is reacted with a mixture of triphenylphosphine and diisopropylazodicarboxylate in an inert solvent such as tetrahydrofuran, ether or toluene at reduced temperatures of from about 0° to about 25° C. to form XIXA

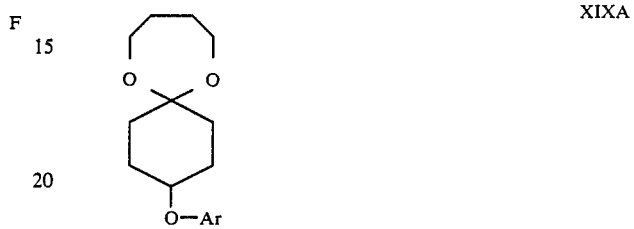

XIXA

Ketal XIX or XIXA is then made to undergo a ketal hydrolysis wherein ketal XIX or XIXA is treated with acetone and water in the presence of pyridinium tosylate and is heated at reflux to form the ketone XX

XX

The ketone XX is subjected to a silyl enol ether formation reaction wherein ketone XX is treated with lithium diisopropylamide in the presence of tetrahydrofuran or ether. The reaction mixture is thereafter treated with trimethylsilyl chloride to form the silyl enol ether XXI

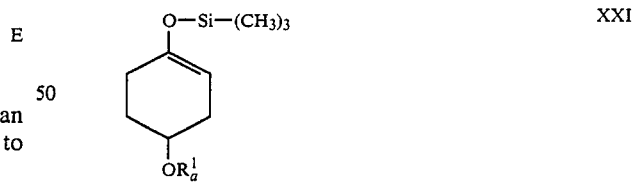

XXI which is made to undergo a condensation reaction wherein a solution of silyl enol ether XXI in dichloromethane is added to a solution of nitroolefin of the structure G

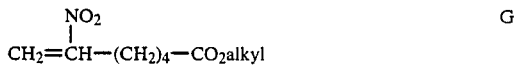

G and $SnCl_4$ in dichloromethane at −78° C. to 0° C., followed by water treatment at 0° C. to reflux to form the ester XXII

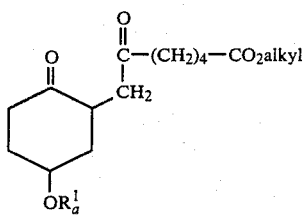
XXII

The ester XXII is then made to undergo a Pschorr pyrrole synthesis as described above to form the ester IH which is hydrolyzed, for example, by treatment with sodium or lithium hydroxide, to form the acid IH'

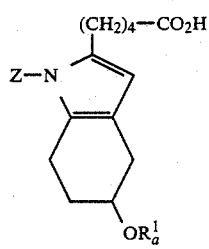
IH'

The nitroolefin G may be prepared by treatment an alkyl 6-heptenoate

H with aqueous mercuric chloride and sodium nitrite and treating the resulting nitro-mercurial with triethylamine and dichloromethane.

Compounds of formula I wherein n is 2, Y is $OR^4$ wherein $R^4$ is alkyl, and X is OH, that is

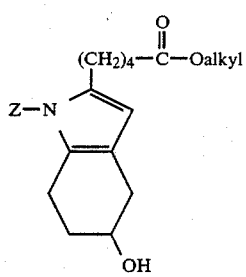
IK may be prepared as follows. Compound IH where $R_a^1$ is benzyl is treated between $-78°$ and $25°$ C. under argon with boron tribromide in dichloromethane to provide IK. The corresponding acid is formed by hydrolysis of ester IK, as described hereinbefore.

Compounds of formula I wherein Z is aryl and X is $-NR^2R^3$ (wherein $R^2$ and $R^3$ are other than Z) may be prepared starting with ID or IK

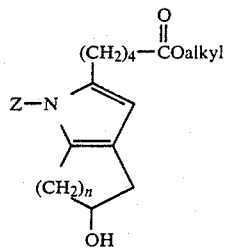

ID (wherein n is 1) or
IK (wherein n is 2)
which is subjected to a Swern oxidation wherein it is reacted with oxalyl chloride in the presence of dimethylsulfoxide to form the ketone XXX

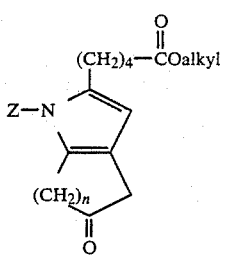
XXX

Ketone XXX is then reacted with the amine J

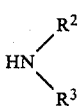
J in the presence of sodium cyanoborohydride and an acid such as hydrochloric acid or acetic acid in methanol to form the amine IL

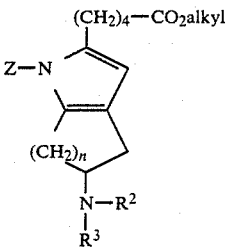
IL which may be hydrolyzed, as described above, to the corresponding acid

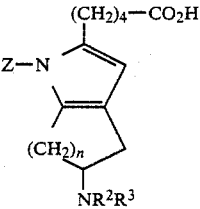
IM

Alternatively, the hydroxy compound ID or IK may be reacted with tosyl chloride in the presence of weak organic base such as pyridine to form the tosylate XXXI

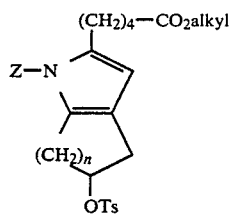

XXXI which is reacted with amine J in the presence of sodium bicarbonate or potassium carbonate in dimethylformamide or hexamethylphosphoric triamide (HMPA) to form the amine IL which may be hydrolyzed to acid IM as described above.

Compounds of formula I wherein Y is —NR$^5$R$^6$, that is

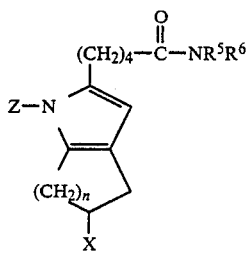

IN may be prepared from the corresponding acid IO as the starting material

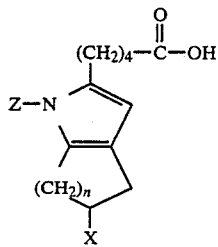

IO

A solution of the acid IO in dichloromethane or other solvent such as ether or tetrahydrofuran under argon is treated with 1-hydroxybenztriazole (HOBT hydrate) and dicyclohexyl carbodiimide (DCC). Thereafter, ammonia (in the case where R$^5$ and R$^6$ are each hydrogen) or amine of the structure

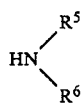

K wherein at least one of R$^5$ and R$^6$ is other than H is added to form compound IN.

Compounds of formula I wherein n is 1 or 2 and Y is OH may be prepared from the corresponding ester

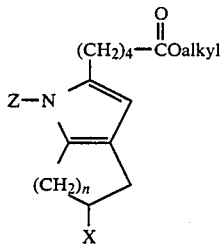

IP by subjecting ester IP to hydrolysis by treating ester IP in solution with aqueous methanol or other lower alcohol with a base such as sodium hydroxide, potassium hydroxide or lithium hydroxide to form the corresponding alkali metal salt, and neutralizing by addition of potassium acid sulfate, dilute hydrochloric acid or oxalic acid to form acid IO

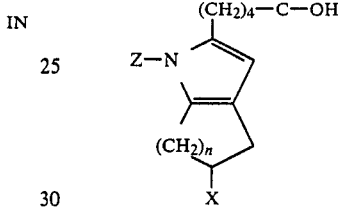

IO

The compounds of the invention prevent arachidonic acid metabolism via the 5-lipoxygenase pathway and also prevent leukotriene formation, (Samuelsson, B., Science, Vol. 220, p. 568–575, 1983). They inhibit the 5-lipoxygenase enzyme from RBL-1 cells and inhibit peptide leukotriene biosynthesis in mouse peritoneal macrophages. The administration of compounds of this invention to humans or animals provides a method for treating allergy of a reagin or non-reagin nature. Asthma is preferably treated but any allergy wherein leukotrienes are thought to be involved as pharmacological mediators of anaphylaxis can be treated. For example, the compounds of this invention can be used for treatment of such conditions as allergic rhinitis, food allergy and urticaria as well as asthma. Further, products of the 5-lipoxygenase pathway have been implicated in psoriasis, and thus the compounds of this invention should be useful in the treatment of psoriasis (S. B. Brain et al., Lancet, p. 762, Oct. 2, 1982).

Metabolites of the 5-lipoxygenase pathway, such as LTB$_4$, have been shown to be potent chemotactic agents for leukocytes, and thus the compounds herein may be effective in various inflammatory states where leukocyte infiltration is important (Samuelsson, supra).

5-Lipoxygenase products have been implicated in essential hypertension (Chand, et al., Microcirculation 1:111–123 (1981)), and gout (Rae, et al., Lancet 1122–1124 (Nov. 20, 1982), indicating that the 5-lipoxygenase inhibitors disclosed herein are useful in treating these conditions as well. Further, neutrophil depletion, such as that induced by 5-lipoxygenase inhibitors, has been shown to cause a significant decrease in infarct size following circumflex artery occlusion. See Romson, et al., Circulation 66: 85 (1982). Thus, the 5-lipoxygenase inhibitors herein may be useful in the protection of the myocardium following infarct.

An effective but essentially non-toxic quantity of the compound is employed in treatment.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the dicussion above, certain members additionally serve as intermediates for other members of the group.

The following Examples represent preferred embodiments of the invention. Unless otherwise indicated, all temperatures are expressed in °C. TLC plates were visualized by spraying and heating with 5% phosphomolybdic acid in ethanol.

EXAMPLE 1

1,4,5,6-Tetrahydro-5-hydroxy-1-phenylcyclopenta[b]pyrrole-2-pentanoic acid, methyl ester

A.

(3aα,4α,5β,6aα)-4-Bromohexahydro-5-hydroxy-2H-cyclopenta[b]furan-2-one

A solution of 9.84 g (48 mmol) of (1α,2α,3β,5α)-2-bromo-3-hydroxybicyclo[3.2.0]heptan-6-one (prepared by the method of Roberts: Z. Grudzinski, S. M. Roberts, *J. C. S. Perkin I* 1975, 1767) in 70 ml of 9:1 acetic acid:water at 0° C. was treated with a chilled solution of 6.3 ml of 30% hydrogen peroxide in 9:1 acetic acid:water and kept at 5° C. for 142 hours. The mixture was diluted with an equal volume of water; the excess peroxide was neutralized with saturated NaHSO$_3$ and extracted with ethyl acetate. The organic extract was washed with water (three portions), saturated NaHCO$_3$ until the washings were basic and then brine. After drying over sodium sulfate, the solution was evaporated and the residue was triturated with ether-hexane to give 7.67 g of a white solid. Recrystallization from dichloromethane-hexane gave 6.1 g of white crystals, m.p. 99°–104° C. TLC silica gel (ether) R$_f$=0.39. This material contained approximately 10% of an isomeric lactone (NMR, IR) which was removed in the following step.

B.

(3aα,5β,6aα)-Hexahydro-5-hydroxy-2H-cyclopenta[b]furan-2-one

A solution of 5.4 g (24.4 mmol) of Part A bromohydrin, 7.2 ml (26.8 mmol) of n-Bu$_3$SnH and 80 mg (0.49 mmol) of azoisobutyronitrile in 100 ml of dry benzene under argon was heated to reflux for 3 hours. The benzene was evaporated at reduced pressure, the residue was taken up in 100 ml of acetonitrile, the acetonitrile solution was washed with six 100 ml portions of hexane. The acetonitrile layer was evaporated to afford 3.26 g of a crude solid, which upon recrystallization from hot benzene containing a small amount of ether, gave 2.67 g (77%) of hydroxy lactone in the form of white crystals: m.p. 77°–79° C. TLC (EtOAc) R$_f$=0.28, single spot. IR (KBr) 3409, 2965, 2931, 2893, 1726, 1380, 1312, 1301, 1214, 1178, 1095, 1029, 985, 977 cm$^{-1}$;

$^1$H NMR(CDCl$_3$) δ 5.07 (t, 1, J=6 Hz), 4.48 (br, 1), 3.03 (m, 1), 2.85 (dd, 1, J=12, 18 Hz), 2.60 (br s, 1), 2.57 (dd, 1, J=3, 12 Hz), 2.22 (d, 1, J=15 Hz), 1.8–2.1 (m, 3) ppm.

$^{13}$C NMR (CDCl$_3$) δ 178.3, 85.6, 73.2, 42.0, 37.1, 36.8 ppm.

Anal calcd for C$_7$H$_{10}$O$_3$: C, 59.14; H, 7.09. Found: C, 58.96; H, 7.06.

C.

(3aα,5β,6aα)-Hexahydro-5-[(tetrahydro-2H-pyran-2-yl)oxy]-2H-cyclopenta[b]furan-2-one To a stirred solution of 2.50 g (17.6 mmol) of Part B ketone in 40 ml of dichloromethane under argon at room temperature was added 2.0 ml (22.0 mmol) of dihydropyran and 200 mg (0.80 mmol) of pyridinium p-tosylate. After stirring for 4 hours, an additional 0.4 ml (4.38 mmol) of dihydropyran was added. After 2.5 hours, the reaction mixture was diluted with dichloromethane and washed with 25 ml of 5% K$_2$CO$_3$. The aqueous layer was extracted with 50 ml of dichloromethane, and the combined organic layers were washed with brine, dried (MgSO$_4$) and evaporated. The crude product was flash chromatographed on silica gel (200 g of LPS-1) eluting with ethyl acetate to afford 3.86 g (97%) of title lactone in the form of a viscous liquid (two diastereomers). TLC (EtOAc) R$_f$=0.44, single spot. IR (CCl$_4$) 2945, 1783, 1178, 1169, 1037, 1022, 1008 cm$^{-1}$.

$^1$H NMR (CDCl$_3$) δ 5.07 and 5.09 (two t, 1, J=6 HZ), 4.65 and 4.70 (two t, J=2.5 Hz), 4.31 and 4.40 (m, 1), 3.66 (m, 1), 3.50 (m, 1), 3.02 (m, 1), 2.3–2.9 (m, 3), 1.4–2.1 (m, 9) ppm.

$^{13}$C NMR (CDCl$_3$) δ 177.7, 177.3, 97.1, 96.1, 85.0, 84.8, 77.5, 76.2, 62.6, 61.7, 40.8, 40.5, 39.2, 37.5, 36.9, 36.7, 36.5, 30.7, 30.5, 25.4, 19.5, 18.7 ppm.

D.

(3aα,5β,6aα)-Hexahydro-5-[(tetrahydro-2H-pyran-2-yl)oxy]-2H-cyclopenta[b]furan-2-ol To a stirred solution of 3.52 g (15.55 mmol) of Part C lactone in 40 ml of dry toluene at −78° C. under argon was added 20 ml of 1M diisobutylaluminum hydride in heptane over 10 minutes. After stirring for 2 hours at −78° C., the reaction was quenched with 0.8 ml (20 mmol) of methanol, and was allowed to warm to 0° C. The reaction mixture was diluted with 120 ml of ether and quenched sequentially with 0.8 ml of water, 0.8 ml of 15% NaOH, and after 15 minutes, 2.4 ml of water. The resulting suspension was allowed to stir for 1 hour at 0° C., some anhydrous Na$_2$SO$_4$ was added, and the solids removed by filtration through Celite. Evaporation of the filtrate afforded 3.53 g (99%) of title lactol in the form of a colorless liquid. TLC (Et$_2$O) R$_f$=0.35, single spot.

E.

[1α(Z),2α,4α]-7-[2-Hydroxy-4-[(tetrahydro-2H-pyran-2-yl)oxy]cyclopentyl]-5-heptenoic acid, methyl ester To a stirred suspension of 898 mg (2.07 mmol) of 4-(carboxybutyl)triphenylphosphonium bromide and 294 mg (1.29 mmol) of Part D lactol in 6 ml of dry toluene at 0° C. under argon was added 2.9 ml (4.14 mmol) of 1.43M potassium t-amyloxide in toluene over 5 minutes. After 15 minutes at 0° C. and then 15 hours at room temperature, the reaction mixture was diluted with 50 ml of ether and washed with 7 ml of 1M KHSO₄ followed by 10 ml of brine. The organic layer was dried (MgSO₄, Na₂SO₄) and evaporated to afford 1.1 g of crude acid in the form of a thick oil.

The crude acid was dissolved in 5 ml of acetone and treated with 0.16 ml (1.69 mmol) of dimethyl sulfate and 202 mg (1.46 mmol) of anhydrous, powdered K₂CO₃. After heating at reflux for 7.5 hours, an additional 100 mg (0.73 mmol) of K₂CO₃ and 0.08 ml (0.84 mmol) of dimethyl sulfate was added, and refluxing was continued for 13 hours. The reaction mixture was partitioned between ether and 5% K₂CO₃, the organic phase was washed with brine, dried (MgSO₄) and evaporated. The crude material was flash chromatographed on silica gel (35 g, Merck-9385) eluting with 50:50 ethyl acetate:hexane to afford 359.2 mg (83%) of pure title cyclopentane as a thick oil.

TLC (50:50 EtOAc:hexane) $R_f$=0.37, single spot.
IR(CCl₄) 3537, 2948, 1741, 1201, 1020, 999 cm⁻¹.
¹H NMR (CDCl₃) δ 5.42 (m, 2), 4.64 (m, 1), 4.36 (m, 1), 4.08 (m, 1), 3.87 (m, 1), 3.67 (s, 3), 3.50 (m, 1), 2.34 (t, 2, J=7 Hz), 1.9–2.3 (m, 18) ppm.

Anal Calcd for C₁₈H₃₀O₅: C, 66.23; H, 9.26. Found: C, 65.68; H, 9.09.

F.
(3aα,5β,6aα)-5-[Hexahydro-5-[(tetrahydro-2H-pyran-2-yl)oxy]-2H-cyclopenta[b]furan-2-yl]-5-iodopentanoic acid, methyl ester To a rapidly stirred, two-phase mixture of 1.51 g (4.6 mmol) of impure Part E cyclopentane compound (contains minor amounts of diol and di-THP) in 60 ml of dichloromethane and 60 ml of saturated NaHCO₃ at 0° C., was added over 2 hours a solution of 1.23 g (4.83 mmol) of I₂ in 60 ml of dichloromethane. The reaction mixture was allowed to stir for an additional hour at 0° C. and then 20 minutes at room temperature. Some 1M Na₂SO₃ was added until the color of I₂ discharged; the organic layer was washed with brine, dried (Na₂SO₄) and evaporated. The crude oil was flash chromatographed on silica gel (175 g, Merck-9385) packed in 20:80 ethyl acetate:hexane and eluted with 37:63 ethyl acetate:hexane, collecting 40 ml fractions. Fractions 10 through 15 afforded 1.22 g (58%) of title compound as a colorless oil. Fractions 45 through 55 afforded 0.51 g (30%) of the corresponding free alcohol (loss of THP). The free alcohol was converted to title compound in 95% yield under standard conditions (1.6 eq. dihydropyran, 0.06 eq. pyridinium tosylate (PPTS), CH₂Cl₂, 0° C. to room temperature), to give an additional 0.59 g of title compound (total yield=87%). TLC (50:50 EtOAc:hexane) $R_f$=0.46, single spot. IR(CCl₄) 2950, 1741, 1200, 1136, 1121, 1077, 1032, 1020 cm⁻¹.

¹H NMR (CDCl₃) δ 4.65 (m, 2), 3.9–4.2 (m, 3), 3.88 (m, 1), 3.68 (s, 3), 3.47 (m, 1), 2.72 (m, 1), 2.33 (t, 2, J=6 Hz), 1.4–2.2 (m, 16) ppm.

G.
(3aα,5β,6aα)-5-[Hexahydro-2-hydroxy-5-[(tetrahydro-2H-pyran-2-yl)oxy]cyclopenta[b]furan-2-yl]pentanoic acid, methyl ester To a stirred solution of 1.52 g (3.36 mmol) of Part F compound in 14 ml of dry benzene at room temperature under argon was added 4.2 ml (34 mmol) of 1,8-diazabicyclo[5.4.0]undec-7-ene. The mixture was allowed to stir for 17 hours at room temperature during which much white solid precipitated. After dilution with 100 ml of ether, the mixture was washed with six 50 ml portions of water (until the water washings were neutral) followed by 30 ml of brine, dried (Na₂SO₄) and evaporated to afford 1.12 g of an oil.

The crude enol ether was dissolved in 14 ml of THF, 1.5 ml of water and 0.24 ml (4.2 mmol) of acetic acid was added, and the reaction mixture was allowed to stir for 3.5 hours at room temperature. After diluting with 100 ml of ethyl acetate, the organic layer was washed successively with two 20 ml portions of saturated NaHCO₃ and 20 ml of brine, dried (Na₂SO₄) and evaporated to afford a crude oil. Flash chromatography on silica gel (150 g, Merck-9385), packed in 40:60 ethyl acetate:hexane and eluted with 80:20 ethyl acetate:hexane, gave 1.06 g (92%) of title compound in the form of a colorless oil. IR indicated that this material exists mainly in the lactol form due to the weak ketone absorption. TLC (75:25 EtOAc:hexane) $R_f$=0.19 (major spot), $R_f$=0.34 (trace, may be open "keto" form). IR (CCl₄) 3600, 3419, 2949, 2270, 1740, 1718 (weak), 1200, 1035, 1019 cm⁻¹.

¹H NMR (CDCl₃) δ 3.84 (m, 1), 3.67 (s, 3), 3.49 (m, 1), 2.33 (t, 2, J=7 Hz) ppm.

H.
(1α,4α)-6-Oxo-7-[2-oxo-4-[(tetrahydro-2H-pyran-2-yl)oxy]cyclopentyl]heptanoic acid, methyl ester A solution of 0.981 g (2.86 mmole) of Part G compound in 8 ml of dry dichloromethane was added to a stirred suspension of 1.23 g (5.72 mmol) of pyridinium chlorochromate and 0.24 g (2.86 mmol) of powdered sodium acetate in 4 ml of dichloromethane. After stirring for 5 hours at room temperature under argon, an additional 0.31 g (1.44 mmol) of pyridinium chlorochromate was added. After 4 hours, the dark suspension was diluted with 125 ml of ether and filtered through a layered plug of MgSO₄ and celite. The filtrate was evaporated to afford a pale brown oil which was purified by flash chromatography on silica gel (150 g, Merck-9385) packed in 30:70 ethyl acetate:hexane, eluted with 65:35 ethyl acetate:hexane to give 0.706 g (72%) of a colorless oil. TLC (Et₂O) $R_f$=0.38, single spot. IR(CCl₄) 2950, 2873, 1743, 1718, 1201, 1154, 1131, 1036 cm⁻¹.

¹H NMR (CDCl₃) δ 4.72 and 4.64 (m, 1), 4.42 (m, 1), 3.86 (m, 1), 3.66 (s, 3), 3.51 (m, 1), 1.4–1.9 and 2.2–3.0 (m, 19) ppm.

¹³C NMR (CDCl₃) δ 216.2, 215.9, 207.9, 173.6, 98.0, 97.6, 72.2, 71.9, 62.63, 62.58, 51.4, 45.5, 44.1, 43.9, 43.6, 42.5, 42.4, 42.3, 36.6, 35.3, 33.7, 30.8, 25.3, 24.3, 23.1, 19.5 ppm.

I.
1,4,5,6-Tetrahydro-5-hydroxy-1phenylcyclopenta[b]pyrrole-2-pentanoic acid, methyl ester To a stirred solution of 102 mg (0.30 mmol) of Part H compound in 1 ml of dry chloroform (through act. I neutral alumina) under argon at room temperature was added 0.28 ml (3.07 mmol) of distilled aniline and 9.5 mg (0.038 mmole) of pyridinium tosylate. The reaction was allowed to stir for 7 hours in the dark when it was diluted with 15 ml of ether, and shaken with 5 ml of 1M KHSO₄. Some water and ethyl acetate were added to dissolve a precipitated solid and dissipate an emulsion. The organic layer was washed with two 5 ml portions of 1M KHSO₄, 5 ml of saturated NaHCO₃ and 5 ml of brine, dried (MgSO₄) and evaporated to afford 115 mg of a yellow oil.

The entire crude product was dissolved in 1 ml of dry methanol (3 Å sieves) under argon, 19 mg (0.075 mmol)

of pyridinium tosylate was added, and the stirred solution heated at 50° C. (bath temperature) in the dark for 12 hours. The near-black solution was partitioned between ethyl acetate and saturated NaHCO$_3$ and the organic layer was washed with brine, dried (MgSO$_4$) and evaporated to give 96 mg of a dark oil. The crude product was flash chromatographed on 8 g of silica gel (Merck-9385) packed in 20:80 ethyl acetate:hexane and eluted with 40:60 ethyl acetate:hexane, collecting 4 ml fractions. Fractions 5 and 6 were combined to afford 10.8 mg of a yellow oil. NMR and TLC indicated that this material was impure 1,4,5,6-tetrahydro-1-phenyl-5-(phenylamino)cyclopenta[b]pyrrole-2-pentanoic acid, methyl ester contaminated with some Part H starting material.

Fractions 10 through 15 were combined to afford 43.3 mg (46%) of title compound as a tan solid: m.p. 83°–85.5° C. TLC (50:50 EtOAc:hexane) R$_f$=0.31. IR (KBr) 3382, 2943, 2845, 1731, 1597, 1500, 1458, 1433, 1387, 1313, 1265, 1239, 1187, 1166, 1046, 771, 705 cm$^{-1}$.

$^1$H NMR (CDCl$_3$) δ 7.43 (t, 2, J=7.5 Hz), 7.31 (t, 1, J=7.5 Hz), 7.22 (d, 2, J=7.5 Hz), 5.86 (s, 1), 4.90 (br m, 1), 3.62 (s, 3), 3.09 (dd, 1, J=6.6, 15 Hz), 2.99 (dd, 1, J=6.9, 15.3 Hz), 2.54 (m, 4), 2.22 (t, 2, J=7.4 Hz), 1.84 (br, 1), 1.55 (m, 4) ppm.

Calcd for C$_{19}$H$_{23}$NO$_3$: C, 72.82; H, 7.40; N, 4.47. Found: C, 72.70; H, 7.44; N, 4.21.

EXAMPLE 2

1,4,5,6-Tetrahydro-5-hydroxy-1-phenylcyclopenta[b]pyrrole-2-pentanoic acid

A solution of 192 mg (0.613 mmol) of Example 1 compound in 3 ml of methanol containing 1.8 ml (1.8 mmol) of 1M NaOH was allowed to stir for 5 hours at room temperature. The mixture was partitioned between 20 ml of dichloromethane and 8 ml of water; the aqueous layer was acidified with 1M KHSO$_4$ and extracted with five 15 ml portions of dichloromethane. The organic layer was washed with brine, dried (MgSO$_4$) and evaporated to afford a yellow semisolid. Recrystallization from dichloromethane/hexane gave 134 mg (64%) title acid in the form of a greyish-white solid containing 0.5 equiv. hexane, by $^1$H NMR, m.p. 112.5°–113.5° C. (changes crystalline form ~75° C.). TLC (EtOAc) R$_f$=0.37. IR (KBr) 3385, 3044, 2927, 2850, 1709, 1597, 1500, 1431, 1389, 1044, 700 cm$^{-1}$.

$^1$H NMR (CDCl$_3$) δ7.43 (t, 2, J=7.2 Hz), 7.33 (t, 1, J=7.2 Hz), 7.22 (d, 2, J=7.2 Hz), 5.86 (s, 1), 4.91 (m, 1), 3.09 (dd, 1, J=6.3, 15.3 Hz), 2.98 (dd, 1, J=6.6, 15.5 Hz), 2.55 (m, 4), 2.26 (t, 2, J=7.1 Hz), 1.55 (m, 4) ppm.

Anal Calcd for C$_{18}$H$_{21}$NO$_3$: C, 72.22; H, 7.07; N, 4.68. Found: C, 72.38; H, 7.10; N, 4.65.

Analytical sample dried at 75° C. under vacuum to remove hexanes.

EXAMPLE 3

1,4,5,6-Tetrahydro-1-phenyl-5-(phenylamino)cyclopenta[b]pyrrole-2-pentanoic acid, methyl ester Impure 1,4,5,6-tetrahydro-1-phenyl-5-(phenylamino)-cyclopenta[b]pyrrole-2-pentanoic acid, methyl ester was obtained as a side product in the preparation of the Example 1 compound. Purification of 60 mg of the impure methyl ester material on 16 g of silica gel (Merck 9385) eluted with 2:98 ethyl acetate:dichloromethane gave 50 mg of pure methyl ester as a pale yellow oil. TLC (5:95 ethyl acetate:dichloromethane) R$_f$=0.58, single spot.

$^1$H NMR (CDCl$_3$) δ 7.41 (t, 2, J=7.5 Hz), 7.31 (t, 1, J=7.5 Hz), 7.24 (d, 2, J=7.5 Hz), 7.15 (t, 2, J=7.5 Hz), 6.68 (t, 1, J=7.5 Hz), 6.60 (d, 2, J=7.5 Hz), 5.87 (s, 1), 4.64 (m, 1), 4.04 (br, 1), 3.62 (s, 3), 3.23 (dd, 1, J=7.4, 14.8 Hz), 3.11 (dd, 1, J=7.1, 15.0 Hz), 2.52 (m, 4), 2.23 (t, 2, J=7.1 Hz), 1.56 (m, 4) ppm.

EXAMPLE 4

1,4,5,6-Tetrahydro-1-phenyl-5-(phenylamino)cyclopenta[b]pyrrole-2-pentanoic acid To 50 mg (0.128 mmol) of Example 3 ester in 4 ml of methanol under argon was added 0.5 ml of 1M NaOH. A white precipitate formed, presumably a result of crystallization of the Example 3 ester. After 3.5 hours at room temperature, 3 ml of i-propanol was added to give a homogeneous solution, followed 1.5 hours later by an additional 0.5 ml 1M NaOH. The reaction mixture was allowed to stir for 18 hours when the solvent was evaporated. The residue was dissolved in water brought to pH 5.5 with KH$_2$PO$_4$ and the aqueous phase was washed with two 20 ml portions of dichloromethane. The organic layer was washed with brine, dried (Na$_2$SO$_4$) and evaporated to afford a foam. Recrystallization from ether-hexane gave 35 mg (67%) of pure title acid as an off-white solid (NMR and combustion analysis indicates that even after 18 hours under vacuum, the off-white solid contained 0.36 eq. of hexane and a trace of ether), m.p. 69°–71° C. TLC (EtOAc) R$_f$=0.5. IR (KBr) 3404, 3049, 2929, 1706, 1599, 1499, 751, 695 cm$^{-1}$.

$^1$H NMR (CDCl$_3$) δ 7.41 (t, 2, J=7.5 Hz), 7.31 (t, 1, J=7.5 Hz), 7.20 (d, 2, J=7.5 Hz), 7.15 (t, 2, J=7.5 Hz), 6.68 (t, 1, J=7.5 Hz), 6.60 (d, 2, J=7.5 Hz), 5.88 (s, 1), 4.64 (m, 1), 3.23 (dd, 1, J=7.4, 14.8 Hz), 3.11 (dd, 1, J=6.9, 14.6 Hz), 2.54 (m, 4), 2.27 (t, 2, J=7.1 Hz), 1.58 (m, 4) ppm.

Anal Calcd for C$_{24}$H$_{26}$N$_2$O$_2$+0.36 equiv. hexane: C, 77.48; H, 7.72; N, 6.91. Found: C, 78.03; H, 8.09; N, 7.04.

EXAMPLE 5

1,4,5,6-Tetrahydro-1-phenyl-5-(phenylmethoxy)cyclopenta[b]pyrrole-2-pentanoic acid, methyl ester

A.

(3aα,5β,6aα)-Hexahydro-5-(phenylmethoxy)-2H-cyclopenta[b]furan-2-one

To a suspension of 1.15 g (28.7 mmol, 1.5 eq.) of 60% NaH dispersion in oil in 30 ml THF at room temperature under argon was added 2.70 g (19.0 mmol) of hydroxylactone prepared as described in Example 1 Part B in 20.0 ml of THF. After having stirred this mixture for 1.5 hours, 352.8 mg (0.95 mmol, 0.05 eq.) of n-Bu$_4$NI and 3.40 ml (28.7 mmol, 1.5 eq.) of benzyl bromide (purified by filtering through alumina) were added in quick succession. Thirty hours later, the reaction was diluted with 150 ml of Et$_2$O and quenched with 5 ml of 10%.HCl. The phases were separated and the organic layer was extracted with 50 ml of Et$_2$O. The combined organic layers were washed with 50 ml of brine, dried over Na$_2$SO$_4$ and evaporated. The crude product was flash chromatographed on silica gel (200 g of LPS-1) eluting with hexane:EtOAc 1:1 to afford 3.09 g (70.1%) of lactone in the form of a colorless oil. TLC silica gel, (EtOAc) R$_f$=0.52. IR (neat) 2935, 1768, 1348, 1206, 1184, 1099, 1058, 1035, 984, 739, 698 cm$^{-1}$.

$^1$H-NMR (CDCl$_3$) δ7.21–7.35 ppm (m, 5), 5.05 (t, 1, J=7 Hz), 4.54, 4.36 (two d, 2, J=12 Hz), 4.08 (br m, 1), 3.00 (m, 1), 2.79 (dd, 1, J=18.5, 10 Hz), 2.49 (dd, 1, J=18.5, 3.5 Hz), 2.42 (d, 1, J=15 Hz), 1.93 (br m, 2), 1.78 (m, 1) ppm.

Mass Spec. (CI—H$_2$O) m/e 233 (M+H$^{\oplus}$), 91.

B.
(3aα,5β,6aα)-Hexahydro-5-(phenylmethoxy)-2H-cyclopenta[b]furan-2-ol

To a stirred solution of 2.97 g (12.8 mmol) of Part A lactone in 30 ml of dry toluene at −78° C. under argon was added 16.5 ml (16.5 mmol, 1.3 eq.) of 1M diisobutylaluminum hydride in heptane. The mixture was stirred for 2 hours at −78° C., quenched with 0.65 ml (16.5 mmol, 1.3 eq.) of methanol and allowed to warm to 0° C. The reaction mixture was diluted with 100 ml of ether and treated sequentially with 0.65 ml of water, 0.65 ml of 15% NaOH, and after 15 minutes, 1.95 ml of water. The resulting suspension was stirred one hour at 0° C., some anhydrous Na$_2$SO$_4$ was added, and the solids were removed by filtration through Celite. Evaporation of the filtrate afforded 2.87 g (96.0%) of title lactol in the form of a colorless liquid. TLC silica gel (EtOAc) R$_f$=0.43, minor impurity R$_f$=0.10.

C.
[1α(Z),2α,4α]-7-[2-Hydroxy-4-(phenylmethoxy)cyclopentyl]-5-heptenoic acid, methyl ester To a stirred suspension of 2.87 g (11.9 mmol) of the Part B lactol and 8.41 g (19.1 mmol, 1.6 eq.) of (4-carboxybutyl)triphenylphosphonium bromide in 55 ml of dry toluene at 0° C. under argon was added 26.8 ml (38.2 mmol, 3.2 eq.) of 1.43M potassium t-amyloxide in toluene over 45 minutes. After an additional 15 minutes at 0° C., the reaction was allowed to warm to room temperature and was stirred for 20 hours. The mixture was diluted with 400 ml of ether, washed with 80 ml of 10% HCl, and 120 ml of brine, dried over Na$_2$SO$_4$ and evaporated to afford 10.36 g of a thick oil.

The crude acid was dissolved in 40 ml of acetone and treated with 2.1 ml (22.2 mmol, 1.87 eq.) of dimethylsulfate and 3.07 g (22.21 mmol) of finely powdered K$_2$CO$_3$. After heating at reflux for 2 hours, the reaction mixture was partitioned between 150 ml of ether and 40 ml of 2M K$_2$CO$_3$. The organic phase was washed with brine, dried over Na$_2$SO$_4$ and evaporated. The crude product was flash chromatographed on silica gel (250 g of LPS-1), eluting with EtOAc:hexane (1:2) to yield 2.50 (63.1%) of the title compound.

$^1$H NMR indicates that this material is contaminated with approximately 0.25 equivalents of dimethyl sulfate.

TLC silica gel (1:1 EtOAc:hexane), R$_f$=0.54, single spot.

IR (neat) 2952, 2866, 1735, 1452, 1393, 1356, 1245, 1200, 1167, 1113, 1062, 1027, 1005, 985, 737, 698 cm$^{-1}$.

$^1$H-NMR (CDCl$_3$) δ7.20–7.40 ppm (m, 5), 5.30–5.52 (m, 2), 4.48 (s, 2), 4.07 (br m, 2), 3.65 (s, 3), 2.37 (br m, 1), 2.30 (t, 2, J=5 Hz), 1.52–2.22 (m, 13) ppm.

Mass Spec. (CI—H$_2$O) m/e 333 (M+H$^{\oplus}$), 207, 127, 107, 91.

D.
(3aα,5β,6aα)-[Hexahydro-5-(phenylmethoxy)-2H-cyclopenta[b]furan-2-yl]-5-iodopentanoic acid, methyl ester To a rapidly stirred, two-phase mixture of 2.50 g (7.25 mmol) of the Part C olefin in 100 ml of CH$_2$Cl$_2$ and 100 ml of saturated NaHCO$_3$ at 0° C. was added over 3 hours a solution of 2.00 g (7.90 mmol, 1.05 eq.) of iodine in 100 ml of CH$_2$Cl$_2$. The reaction mixture was allowed to stir for an additional hour at 0° C. then 30 minutes at room temperature. Some 1M Na$_2$SO$_3$ was added until the color of I$_2$ was discharged. The organic layer was washed with brine, dried over Na$_2$SO$_4$ and evaporated for a crude yield of 3.30 g (96.0%).

TLC silica gel (1:1 EtOAc:hex) R$_f$=0.66, single spot.

E.
(3aα,5β,6aα)-[Hexahydro-5-(phenylmethoxy)-2H-cyclopenta[b]furan-2-yl]-5-hydroxypentanoic acid, methyl ester To a solution solution of 3.30 g (7.20 mmol) of Part D iodo compound in 30 ml of dry benzene at room temperature under argon was added 9.00 ml (72.8 mmol) of 1,8-diazabicyclo[5.4.0]undec-7-ene (DBU). The mixture was allowed to stir for 15 hours at room temperature. After dilution with 200 ml of ether, the mixture was washed with four 100 ml portions of water (until the water washings were neutral) followed by 65 ml of brine, dried over Na$_2$SO$_4$ and evaporated.

The crude enol ether was dissolved in 30 ml of THF, 3.2 ml of water and 0.51 ml (9.0 mmol) of glacial acetic acid were added and the reaction mixture was allowed to stir for 3.5 hours at room temperature. After diluting with 200 ml of EtOAc, the organic layer was washed successively with two 40 ml portions of saturated NaHCO$_3$ and 40 ml of brine, dried over Na$_2$SO$_4$ and evaporated to yield 2.35 g (93.6%) of crude product.

Flash chromatography on silica gel (250 g of LPS-1), eluting with 1:1 hexane:EtOAc followed by 1:2 hexane:EtOAc afforded 1.80 g (72%) of the title lactol. TLC silica gel (1:1 EtOAc:hex), R$_f$=0.23 (major spot), R$_f$=0.44 (minor spot).

F.
(1α,4α)-6-Oxo-7-[2-oxo-4-(phenylmethoxy)cyclopentyl]heptanoic acid, methyl ester A solution of 1.50 g (4.3 mmol) of Part E lactol in 12.0 ml of CH$_2$Cl$_2$ was added to a suspension of 1.845 g (8.58 mmol, 2 eq.) of pyridinium chlorochromate and 375 mg (4.3 mmol) of finely powdered sodium acetate in 6.0 ml of CH$_2$Cl$_2$. After stirring for 7.5 hours at room temperature under argon an additional 461 mg (0.5 eq., 2.15 mmol) of pyridinium chlorochromate was added to the reaction mixture. Sixteen hours later, 400 ml of ether was added and the reaction stirred for 0.5 hour, then some MgSO$_4$ was added and the reaction was stirred for 15 minutes, before filtering through a celite pad and washing copiously with ether. Evaporation afforded 1.49 g of crude product. Purification by flash chromatography on LPS-1 silica gel (150 g), eluting with hexane:EtOAc 4:3 yielded 919 mg (61.7%) of the desired title diketone as a colorless oil. TLC: silica gel (EtOAc:hexane 1:1) R$_f$=0.31, single spot.

IR (neat) 2948, 2970, 1739, 1710, 1451, 1434, 1407, 1355, 1246, 1201, 1155, 1099, 738, 699 cm$^{-1}$.

$^1$H NMR (CDCl$_3$) δ7.28–7.38 ppm (m, 5), 4.54 (s, 2), 4.21 (m, 1), 3.66 (s, 3), 2.90 (br d, 1, J=14 Hz), 2.20–2.80 (m, 8), 1.55–1.70 (m, 6) ppm.

Mass Spec. (CI—H$_2$O) m/e 347 (M+H$^{\oplus}$), 329, 315, 239, 207.

G.
1,4,5,6-Tetrahydro-1-phenyl-5-(phenylmethoxy)cyclopenta[b]pyrrole-2-pentanoic acid, methyl ester To a solution of 300 mg (0.87 mmol) of Part F diketone and 383 μL (6.5 mmol, 7.5 eq.) of aniline in 3.0 mL of dry CH$_2$Cl$_2$ at 0° C. under argon in the dark, was added 115 μL (1.05 mmol, 1.2 eq.) of TiCl$_4$ in a dropwise manner. After stirring at 0° C. for 1 hour the solution was allowed to warm to room temperature and stirred for 18 hours. The reaction mixture was taken up in 90 ml of hexane, washed with three 30 mL portions of 10% HCl, 30 ml of saturated NaHCO$_3$, and 30 ml of saturated brine, dried over Na$_2$SO$_4$ and evaporated for a crude yield of 255.5 mg. Purification by flash chromatography on silica gel (30 g Merck-9385), eluting with hexane:Et$_2$O 3:1 gave 148.2 mg (42.8%) of the desired pyrrole as a pale yellow oil. TLC silica gel (hexane:Et$_2$O 3:1) R$_f$=0.27 single spot.

IR (film) 2930, 1735, 1597, 1499, 1450, 1433, 1216, 1173, 1089, 1071, 752, 698 cm$^{-1}$.

$^1$H-NMR(CDCl$_3$) (270 MHz) δ7.20–7.45 ppm (m, 10), 5.84 (s, 1), 4.70 (m, 1), 4.54 (s, 2), 3.61 (s, 3), 3.02 (dd, 1, J=14.5, 7 Hz), 2.97 (dd, 1H, J=14.5, 7 Hz), 2.77 (dd, 1H, J=10.5, 5 Hz), 2.74 (dd, 1H, J=10.5, 5 Hz), 2.51 (t, 2H, J=7.5 Hz), 2.21 (t, 2H, J=7.5 Hz), 1.40–1.65 (m, 4H) ppm.

Mass Spec. (CI—H$_2$O) m/e 404 (M+H$^\oplus$), 372, 312, 296.

EXAMPLE 6

1,4,5,6-Tetrahydro-1-phenyl-5-(phenylmethoxy)cyclopenta[b]pyrrole-2-pentanoic acid To a solution of 148.0 mg (0.37 mmol) of Example 5 ester in 15 ml of i-PrOH under argon in the dark was added 1.48 ml (1.48 mmol, 4 eq.) of 1M NaOH. The resulting mixture was stirred at room temperature for 22 hours, when the solvent was removed under reduced pressure. The residue was rapidly stirred with 10 ml of H$_2$O and 10 ml of CH$_2$Cl$_2$ and acidified with 10% HCl. The aqueous phase was extracted with two 50 ml portions of CH$_2$Cl$_2$. The combined organic layers were dried over MgSO$_4$ and evaporated, affording 131.5 mg of crude acid as a tan solid. Flash chromatography on silica gel (15 g Merck-9395), eluting with 60:40 Et$_2$O:-hexane yielded 100.4 mg (69.9%) of the desired acid as light tan crystals, m.p. 93°–94° C.

TLC Silica gel (3:7 EtOAc:hex), R$_f$=0.21 single spot.
IR(KBr) 3427, 2943, 2859, 1708, 1596, 1499, 1428, 1389, 1345, 1271, 1187, 1072, 759, 732, 695 cm$^{-1}$.

$^1$H-NMR (CDCl$_3$) δ7.20–7.44 (m, 10), 5.84 (s, 1), 4.69 (m, 1), 4.55 (s, 2), 3.01 (dd, 1, J=14, 7 Hz), 2.97 (dd, 1, J=14, 7 Hz), 2.78 (dd, 1, J=10, 5 Hz), 2.72 (dd, 1, J=10, 5 Hz), 2.51 (t, 2, J=7.5 Hz), 2.25 (t, 2, J=7.5 Hz), 1.49–1.65 (m, 4) ppm.

$^{13}$C-NMR (CDCl$_3$) δ178.2, 139.3, 138.6, 136.1, 133.7, 129.1, 128.3, 127.7, 127.5, 126.9, 126.2, 121.6, 102.4, 83.7, 71.1, 33.6, 33.5, 33.2, 28.8, 26.9, 24.3 ppm.

Mass Spec. (CI—H$_2$O) m/e 390 (M+H$^\oplus$), 372, 282.
Anal Calcd for C$_{25}$H$_{27}$NO$_3$: C, 77.09; H, 6.98; N, 3.60. Found: C, 77.07; H, 7.04; N, 3.55.

EXAMPLE 7

4,5,6,7-Tetrahydro-1-phenyl-5-(phenylmethoxy)-1H-indole-2-pentanoic acid

A. 7,12-Dioxaspiro[5.6]dodecan-3-one (Ref.: Hyatt, G. A.; *J. Org. Chem.*, 1983, 48, 129)

To a stirred solution of 56.0 g (0.5 mol) of 1,4-cyclohexanedione, and 0.25 g (1.3 mmol) of p-toluenesulfonic acid in 500 ml of toluene under argon, refluxing with a Dean-Stark trap was added 44.5 ml (0.5 mol, 1 eq.) of freshly distilled 1,4-butanediol over 3.5 hours. After refluxing for an additional hour, the mixture was allowed to cool, then washed with 20 ml of saturated NaHCO$_3$, dried over MgSO$_4$ and evaporated. The residue was triturated with an equal volume of EtOAc and cooled in ice. The precipitated bis-ketal was removed by filtration and the solvent was evaporated from the filtrate. Separation of the diketone from the desired ketal was accomplished by three successive distillations, the last two using a 12 inch Vigreux column. This procedure afforded 16.74 g (18%) of title monoketal (b.p. 80°–81° C./0.5 mm) as a colorless, viscous liquid. A trace of cyclohexanedione was present. TLC silica gel (EtOAc), R$_f$0.51.

$^1$H-NMR (CDCl$_3$) δ 3.62 (br s, 4), 2.27 (t, 4H, J=7 Hz), 1.87 (t, 4H, J=7 Hz), 1.53 (m, 4H) ppm.

B. 3-(Phenylmethoxy)-7,12-dioxaspiro[5.6]dodecane

To a well-stirred suspension of 1.70 g (0.045 mol, 2 eq.) of lithium aluminum hydride in 120 ml of Et$_2$O at 0° C. under argon was added 16.50 g (0.09 mol) of Part A ketone in 30 ml of Et$_2$O in a dropwise manner. The reaction was quenched immediately following the addition by treating sequentially with 1.70 ml of water, 1.70 ml of 15% NaOH and, after 15 minutes, 5.10 ml of water. After stirring at 0° C. for 1 hour, the reaction mixture was filtered through Celite, washing well with Et$_2$O. Removal of the solvent afforded 16.16 g (96%) of the alcohol as a viscous oil.

To a vigorously stirred suspension of 2.16 g (54 mmol) of 60% NaH dispersion in oil in 30 ml of THF under argon at 0° C. was added 5.00 g (27 mmol) of the crude alcohol. After stirring at 0° C. for 45 minutes and at room temperature for one hour, this solution was treated in rapid succession with 995 mg (2.7 mmol, 0.1 eq.) of tetra-n-butylammonium iodide in 20 ml of THF and 4.20 ml (35 mmol, 1.3 eq.) of benzyl bromide. After stirring overnight, the reaction mixture was carefully quenched with water, then partitioned between 100 ml of Et$_2$O and 50 ml of saturated NaHCO$_3$. The organic phase was washed with 50 ml of brine, dried over Na$_2$SO$_4$ and evaporated. The product was purified by bulb-to-bulb distillation (180°–190° C./0.15 mm) to provide 7.01 g (91%, overall yield from Part A ketone) of title ketal in the form of a colorless liquid. TLC silica gel (1:1 Et$_2$O:hexane) R$_f$=0.47, single spot.

$^1$H-NMR (CDCl$_3$) δ 7.34–7.12 (m, 5), 4.45 (s, 2), 3.60 (m, 4), 3.42 (m, 1), 1.35–1.90 (m, 12) ppm.

C. 4-(Phenylmethoxy)cyclohexanone

A solution of 6.80 g (24.6 mmol) of Part B ketal and 1.85 g (7.38 mmol, 0.3 eq.) of pyridinium p-toluenesulfonate in 250 ml of acetone and 10 ml of water was heated at reflux for three hours. After cooling to room temperature, the solvent was removed under vacuum. The residue was taken up in 800 ml of Et$_2$O and was washed with 200 ml of saturated NaHCO$_3$ and 200 ml of brine, dried over Na$_2$SO$_4$ and evaporated. Purification by bulb-to-bulb distillation, collecting at 130°–150° C./0.1 mm, afforded 4.48 g (89%) of title ketone in the form of a colorless oil, which solidifies below room temperature.

TLC silica gel (1:1 Et$_2$O:hexane) R$_f$=0.34, single spot.

$^1$H-NMR(CDCl$_3$) δ7.27–7.18 (m, 5), 4.49 (s, 2), 3.71 (m, 1), 2.52 (m, 2), 2.18 (m, 2), 2.03 (m, 2), 1.86 (m, 2) ppm.

D.
4-(Phenylmethoxy)-1-[(trimethylsilyl)oxy]cyclohexene

To a solution of 0.40 ml (2.8 mmol), 1.4 eq.) of diisopropylamine in 4.0 ml of THF at −78° C. under argon was added 1.54 ml (2.4 mmol, 1.2 eq.) of 1.57M n-butyllithium in hexane solution. The solution was warmed to 0° C. for 10 minutes, recooled to −78° C. and treated with a solution of 408 mg (2.0 mmol) of Part C ketone in 3.0 ml of THF over 8 minutes. After stirring for 0.5 hour at −78° C., the reaction mixture was quenched with 0.40 ml (3.2 mmol, 1.6 eq.) of freshly distilled trimethylsilyl chloride, added over 2 minutes. Subsequent to having been at −78° C. for 20 minutes, at 0° C. for 1 hour and at room temperature for 0.5 hour, the solvent was evaporated. The residue was evaporated with dry hexane, triturated with dry hexane and filtered. The filtrate was evaporated to obtain 552.0 mg (99%) of a viscous, colorless liquid. TLC silica gel (2:8 Et$_2$O-hexane) R$_f$=0.55, single spot.

$^1$H-NMR (CDCl$_3$) δ 7.34–7.25 (m, 5), 4.72 (m, 1), 4.56 (s, 2), 3.62 (m, 1), 2.33 (m, 1), 2.11 (m, 3), 1.95 (m, 1), 1.79 (m, 1), 0.17 (s, 9) ppm.

E. 6-Nitro-6-heptenoic acid, methyl ester

To 32 ml of distilled water was added 3.42 g (12.6 mmol) of mercuric chloride followed by 5.2 g (75.6 mmol) of sodium nitrite, resulting in a pale yellow solution. After 10 minutes, 1.5 g (10.6 mmol) of methyl 6-heptenoate was added, and the mixture allowed to stir rapidly for 24 hours. The suspension was partitioned between brine and dichloromethane; the organic layer was washed with brine, dried (CaCl$_2$) and evaporated to give 4.3 g of the crude β-nitro mercurial as a thick, pale-yellow oil.

This material was dissolved in 20 ml of dry dichloromethane under argon at room temperature, and 1.5 ml (11 mmol) of triethylamine was added dropwise over 4 minutes. After 45 minutes, the solution was diluted with 10 ml of dichloromethane and 125 ml of petroleum ether, and decanted from the metallic mercury. The organic layer was washed with three 25 ml portions of 10% HCl, 25 ml of water, and 25 ml of brine, dried (MgSO$_4$) and evaporated to afford a yellow liquid. Bulb-to-bulb distillation (130°–150° C., 0.05 mm) of the crude material gave 1.06 g (53%) of title nitro-olefin as a pale yellow liquid. $^1$H NMR suggests that the title nitro-olefin in the form of the pale yellow liquid contains approximately 6% of the regio-isomeric nitro olefin.

TLC silica gel (40:60 ethyl acetate:hexane) R$_f$=0.52, single spot.

IR (CCl$_4$) 2952, 2865, 1741, 1529, 1457, 1434, 1344, 1241, 1197, 1173, 938 cm$^{-1}$.

$^1$H NMR (CDCl$_3$) δ6.41 (d, 1, J=2 Hz), 5.54 (br s, 1), 3.66 (s, 3), 2.60 (t, 2, J=7.5 Hz), 2.34 (t, 2, J=7 Hz), 1.45–1.80 (m, 4) ppm.

Anal Calcd for C$_8$H$_{13}$NO$_4$: C, 51.33; H, 7.00; N, 7.48. Found: C, 51.01; H, 6.98; N, 7.31.

F. 6-Oxo-7-[2-oxo-5-(phenylmethoxy)cyclohexyl]heptanoic acid, methyl ester

A solution of 562.3 mg (3 mmol) of Part E nitro-olefin in 4.5 ml of dry CH$_2$Cl$_2$ at −78° C. under argon was treated with 0.405 ml (3.45 mmol) of SnCl$_4$ and stirred for 25 minutes. A solution of 1.10 g (3.94 mmol, 1.3 eq.) of the part E enol ether in 4.5 ml of CH$_2$Cl$_2$ was added over 30 minutes and the resulting mixture was stirred at −78° C. for 1 hour. After allowing the solution to warm gradually over 2.5 hours to 0° C. and to stir at 0° C. for 0.5 hour, the mixture was treated with 6.0 ml of H$_2$O and refluxed for 3 hours. The reaction mixture was diluted with 75 ml of CH$_2$Cl$_2$, washed with 20 ml of brine, dried over MgSO$_4$ and evaporated for a crude yield of 1.99 g of a dark brown oil. Purification by flash chromatography on 200 g LPS-1 silica gel eluted with Et$_2$O:petroleum ether 1:1, gave 563 mg (52%) of pure title ester as a yellow oil.

TLC silica gel (1:1 EtOAc:Hex), R$_f$0.37, single spot.

IR (neat) 3335, 2927, 2853, 1732, 1708, 1658, 1530, 1451, 1434, 1405, 1065, 739, 698 cm$^{-1}$.

$^1$H-NMR (CDCl$_3$) δ 7.38–7.28 (m, 5), 4.61 (m, 2), 3.89 (m, 1), 3.66 (s, 3), 1.4–3.5 (various m, 17) ppm.

Mass Spec. (CI—H$_2$O) m/e 361 (M+H$^\oplus$), 343, 329, 253.

G. 4,5,6,7-Tetrahydro-1-phenyl-5-(phenylmethoxy)-1H-indole-2-pentanoic acid

To a solution of 300.0 mg (0.83 mmol) of Part G ester in 4.2 ml of CHCl$_3$ (passed through neutral alumina) under argon at room temperature was added 0.705 ml (8.3 mmol, 10 eq.) of aniline and 42 mg (0.17 mmol, 0.2 eq.) of pyridinium p-tolunesulfonate. The mixture was stirred in the dark for 7 hours, then taken up in 50 ml of EtOAc, washed with three 20 ml portions of 10% HCl, 20 ml of saturated NaHCO$_3$ and 20 ml of brine, dried over MgSO$_4$ and evaporated to yield 321.4 mg of crude ester.

TLC silica gel (2:1 Et$_2$O:hexane) R$_f$=0.63 and baseline spot.

A solution of 310.2 mg (0.74 mmol) of the crude ester in 30 ml of isopropanol in the dark under argon was treated with 3.0 ml (3.0 mmol) of 1M NaOH. The resultant mixture was stirred at room temperature for 24 hours and the solvent was removed under vacuum. The residue was taken up in 75 ml of H$_2$O and 75 ml of CH$_2$Cl$_2$ and acidified with 20 ml of 10% HCl. The aqueous layer was extracted with two 50 ml portions of CH$_2$Cl$_2$. The combined organic phases were washed with 20 ml of brine, dried over MgSO$_4$ and evaporated for a crude yield of 265.2 mg (89%). Purification by flash chromatography on 50 g of Merck 9385 silica gel, eluted with 2:1 Et$_2$O:petroleum ether gave 190.1 mg (64%) of a white solid. An analytically pure sample was obtained by trituration with hexane, to afford, upon drying under vacuum, 139.3 mg of title product in the form of white crystals, m.p. 88°–89° C. TLC silica gel (7:3 Et$_2$O:hexane) R$_f$=0.40, single spot.

IR (KBr) 2940, 2841, 1713, 1595, 1496, 1428, 1409, 1381, 1306, 1252, 1197, 1091, 1071, 730, 699 cm$^{-1}$.

$^1$H-NMR (CDCl$_3$) δ7.17–7.45 (m, 10), 5.81 (s, 1), 4.63 (s, 2), 3.83 (m, 1), 2.96 (dd, 1, J=15.0, 5.5 Hz), 2.61 (dd, 1, J=15.0, 8.5 Hz), 2.39 (br, 4), 2.24 (t, 2, J=7.0 Hz), 2.05 (m, 1), 1.84 (m, 1), 1.55 (m, 4) ppm.

$^{13}$C-NMR (CDCl$_3$) δ178.5, 139.0, 138.6, 133.1, 129.0, 128.3, 127.9, 127.6, 127.5, 127.4, 127.0, 114.2, 105.0, 75.3, 70.3, 33.5, 29.6, 28.9, 28.5, 26.4, 24.3, 21.0 ppm.

Mass Spec. (CI—H$_2$O) m/e 404 (M+H$^\oplus$), 296, 294.

Anal Calcd for C$_{26}$H$_{29}$NO$_3$ (MW403.525): C, 77.39; H, 7.24; N, 3.47. Found: C, 77.04; H, 7.23; N, 3.27.

EXAMPLES 8 TO 30

The followng additional compounds may be prepared following the procedures set out above and in the working Examples.

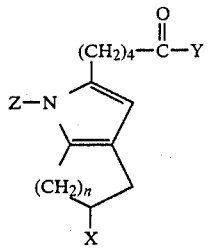

| Ex. No. | n | X | Z | Y |
|---|---|---|---|---|
| 8. | 1 | —OC₂H₅ | C₆H₅ | OH |
| 9. | 1 | —(CH₂)₉CH₃ | C₆H₅ | OH |
| 10. | 1 | —O—⟨cyclopentyl⟩ | C₆H₅ | OH |
| 11. | 1 | —OCH₂C₆H₅ | p-Cl—C₆H₅ | OH |
| 12. | 1 | —O(CH₂)₂C₆H₅ | C₆H₅ | OC₂H₅ |
| 13. | 1 | —O—⟨naphthyl⟩ | C₆H₅ | OH |
| 14. | 1 | —OCH₂C₆H₅ | ⟨methylnaphthyl⟩ | N(CH₃)₂ |
| 15. | 1 | —NHCH₂C₆H₅ | C₆H₅ | OH |
| 16. | 1 | —N(CH₃)(CH₂C₆H₅) | C₆H₅ | OH |
| 17. | 1 | —NH—⟨cyclopentyl⟩ | p-CH₃O—C₆H₅ | OCH₃ |
| 18. | 1 | —NHC₆H₅ | p-CH₃—C₆H₅ | —NH(CH₂C₆H₅) |
| 19. | 1 | —N(CH₃)(C₆H₅) | C₆H₅ | N(CH₃)₂ |
| 20. | 1 | —O(CH₂)₄C₆H₅ | C₆H₅ | OH |
| 21. | 1 | —O(CH₂)₈CH₃ | C₆H₅ | NH₂ |
| 22. | 1 | —O(CH₂)₄C₆H₅ | C₆H₅ | N(CH₃)₂ |
| 23. | 1 | —OC₆H₅ | C₆H₅ | OH |
| 24. | 2 | O(CH₂)₄—⟨cyclohexyl⟩ | C₆H₅ | OH |
| 25. | 2 | O(CH₂)₄C₆H₅ | C₆H₅ | NH₂ |
| 26. | 2 | OC₆H₅ | C₆H₅ | OH |
| 27. | 2 | OCH₂C₆H₅ | ⟨methylnaphthyl⟩ | OH |
| 28. | 2 | OCH₂—⟨naphthyl⟩ | C₆H₅ | OH |
| 29. | 2 | NH(CH₂)₇CH₃ | C₆H₅ | N(CH₃)₂ |
| 30. | 2 | NHC₆H₅ | C₆H₅ | OH |

What is claimed is:

1. A compound having the structure $$\text{(structure shown)}$$

wherein n is 1 or 2;
X is —OR¹ or —NR²R³ wherein R¹ is H, lower alkyl, cycloalkyl, aryl, aralkyl or cycloalkylalkyl, and R² and R³ may be the same or different and are H, lower alkyl, cycloalkyl, aryl, aralkyl or cycloalkylalkyl;
Y is —OR⁴ or —NR⁵R⁶ wherein R⁴ is H or lower alkyl, and R⁵ and R⁶ are the same or different and are H or lower alkyl; and Z is aryl; wherein the term lower alkyl or alkyl by itself or as part of another group contains 1 to 12 carbons and is unsubstituted or substituted with halo, CF₃, alkoxy, aryl, alkyl-aryl, haloaryl, cycloalkyl or alkylcycloalkyl, the term aryl or "ar" by itself or as part of another group refers to monocyclic or bicyclic aromatic groups containing from 6 to 10 carbons and is unsubstituted or is substituted with 1 or 2 halogens, 1 or 2 lower alkyl groups and/or 1 or 2 lower alkoxy groups, and the term cycloalkyl by itself or as part of another group refers to saturated cyclic hydrocarbon groups containing 3 to 8 carbons in the ring and is unsubstituted or is substituted with 1 or 2 halogens, 1 or 2 lower alkyl groups and/or 1 or 2 lower alkoxy groups.

2. The compound as defined in claim 1 wherein Z is phenyl.

3. The compound as defined in claim 1 wherein n is 1, Z is phenyl, Y is OH or alkoxy, and X is OH, alkoxy, benzyloxy or —NHC₆H₅.

4. The compound as defined in claim 1 wherein n is 2, Z is phenyl, Y is OH or alkoxy, and X is OH, alkoxy or benzyloxy.

5. The compound as defined in claim 1 wherein n is 1, Z is phenyl, Y is OH or methoxy, and X is OH, —OCH₂C₆H₅ or —NHC₆H₅.

6. The compound as defined in claim 1 having the name 1,4,5,6-tetrahydro-5-hydroxy-1-phenylcyclopenta[b]pyrrole-2-pentanoic acid or its methyl ester.

7. The compound as defined in claim 1 having the name 1,4,5,6-tetrahydro-5-hydroxy-1-phenylcyclopenta[b]pyrrole-2-pentanoic acid.

8. The compound as defined in claim 1 having the name 1,4,5,6-tetrahydro-1-phenyl-5-(phenylamino)cyclopenta[b]pyrrole-2-pentanoic acid.

9. The compound as defined in claim 1 having the name 1,4,5,6-tetrahydro-1-phenyl-5-(phenylmethoxy)-cyclopenta[b]pyrrole-2-pentanoic acid.

10. The compound as defined in claim 1 having the name 4,5,6,7-tetrahydro-1-phenyl-5-(phenylmethoxy)-1H-indole-2-pentanoic acid.

11. A composition for inhibiting allergic conditins of a reagin or non-reagin nature wherein leukotrienes are involved as pharmacological mediators of anaphylaxis, in a mammalian species, comprising an effective amount of a compound as defined in claim 1 or a pharmaceutically acceptable salt thereof, and a pharmaceutically acceptable carrier therefor.

12. The composition as defined in claim 11 wherein said compound is administered in an amount within the range of from about 1 to about 100 mg/kg.

13. A method for treating asthma mediated by leukotrienes in a mammalian species in need of such treatment, which comprises administering to a mammalian host an effective amount of a compound as defined in claim 1 or a pharmaceutically acceptable salt thereof.

14. A method for treating inflammation involving leukocyte infiltration, in a mammalian species in need of such treatment, which comprises administering to a mammalian host an effective amount of a compound as defined in claim 1 or a pharmaceutically acceptable salt thereof.

* * * * *